(12) United States Patent
Schambon

(10) Patent No.: US 9,211,220 B2
(45) Date of Patent: Dec. 15, 2015

(54) DIAPERING ASSISTANCE SYSTEM AND METHOD

(71) Applicant: Amanda N Schambon, Blue Bell, PA (US)

(72) Inventor: Amanda N Schambon, Blue Bell, PA (US)

(*) Notice: Subject to any disclaimer, the term of this patent is extended or adjusted under 35 U.S.C. 154(b) by 98 days.

(21) Appl. No.: 14/084,805

(22) Filed: Nov. 20, 2013

(65) Prior Publication Data

US 2014/0163513 A1   Jun. 12, 2014

Related U.S. Application Data

(60) Provisional application No. 61/797,405, filed on Dec. 6, 2012.

(51) Int. Cl.
| | | |
|---|---|---|
| *A61F 13/15* | (2006.01) | |
| *A61F 13/56* | (2006.01) | |
| *A61F 13/505* | (2006.01) | |
| *A61F 13/64* | (2006.01) | |
| *A61F 13/72* | (2006.01) | |
| A61F 13/66 | (2006.01) | |
| A61F 13/74 | (2006.01) | |

(52) U.S. Cl.
CPC ........... *A61F 13/5622* (2013.01); *A61F 13/505* (2013.01); *A61F 13/64* (2013.01); *A61F 13/72* (2013.01); *A61F 13/66* (2013.01); *A61F 13/74* (2013.01)

(58) Field of Classification Search
CPC ....... A61F 13/505; A61F 13/64; A61F 13/66; A61F 13/68; A61F 13/70; A61F 13/72; A61F 13/74; A61F 13/76; A61F 13/78; A61F 13/80; A61F 13/82

USPC .................. 604/402, 392, 393, 394, 395, 396, 604/397–401

See application file for complete search history.

(56) References Cited

U.S. PATENT DOCUMENTS

| | | | | |
|---|---|---|---|---|
| 4,280,230 A | * | 7/1981 | LaFleur | 2/408 |
| 4,338,939 A | * | 7/1982 | Daville | 604/399 |
| 4,761,834 A | * | 8/1988 | Kolb | 2/465 |
| 5,445,628 A | * | 8/1995 | Gipson et al. | 604/392 |
| 5,906,604 A | * | 5/1999 | Ronnberg et al. | 604/386 |
| 7,195,622 B2 | * | 3/2007 | Lindstrom | 604/392 |
| 2005/0192555 A1 | * | 9/2005 | Thomas | 604/402 |
| 2006/0247599 A1 | * | 11/2006 | Mullen et al. | 604/393 |

OTHER PUBLICATIONS www.dictionary.reference.com/browse/belt, 20150408.*

* cited by examiner

*Primary Examiner* — Lynne Anderson
*Assistant Examiner* — Bradley Philips
(74) *Attorney, Agent, or Firm* — Stuart M. Goldstein

(57) ABSTRACT

A diapering assistance system utilizes a diaper and a diaper holding member which retains the top end of the diaper and suspends its bottom end. A belt member attached to the diaper holding member, encircles the waist of the individual being diapered. The belt member has connection devices, such as hook and loop connectors, and constitutes the sole component used for attaching the system to the individual. The method of use includes securing the top end of the diaper to the diaper holding member, suspending the diaper therefrom and behind the individual to be diapered, encircling the individual with the belt element, and securing it around the individual's waist. The bottom end of the diaper is then lifted between the legs and to the front of the individual. The diaper is attached to the individual and the diaper holding member and belt member are removed.

4 Claims, 5 Drawing Sheets

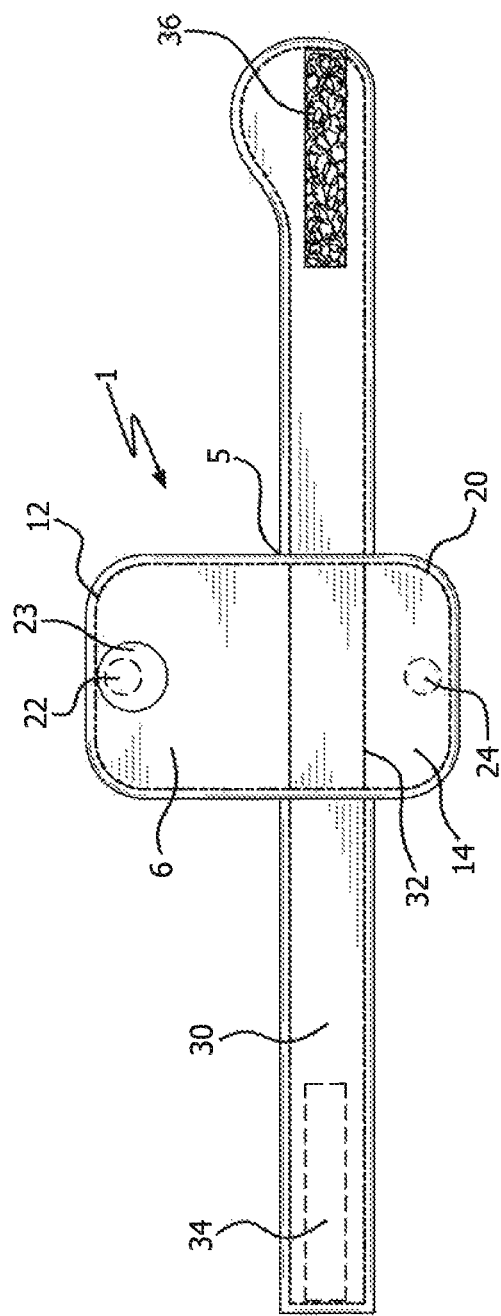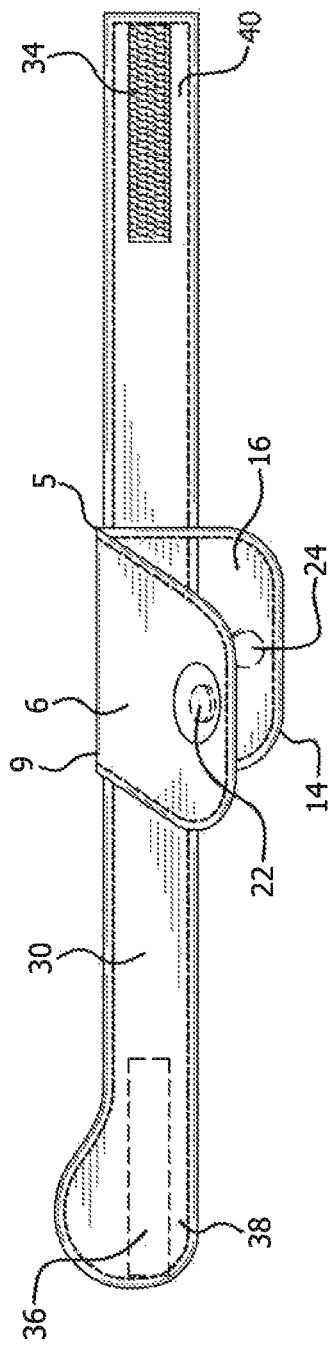
FIG. 1
FIG. 2

DIAPERING ASSISTANCE SYSTEM AND METHOD

RELATED APPLICATION

The herein application claims the benefit of provisional application Ser. No. 61/797,405 filed on Dec. 6, 2012.

BACKGROUND OF THE INVENTION

Diapering infants and small children is routinely done by placing the child on his or her back, usually on a diapering pad or similar soft surface, lifting the legs and positioning the diaper beneath the child. This tried and true method is effective, except when there is little room to spread out a pad or even when attempting to position a child to be diapered in a prone position. There is currently no easy and effective way to diaper a baby while he or she is upright or crawling and no easy, effective, and unobtrusive way to apply diapers to older individuals who must wear them.

SUMMARY OF THE INVENTION

It is thus the object of the present invention to provide a diapering assistance system which is designed to assist in applying diapers to all individuals, including babies and others who find it necessary to wear diapers.

For babies, age three months to twenty four months, the current invention allows diapering while the children are in standing or crawling positions. It permits a parent to change the baby's diaper without the necessity of having the baby lie down. In addition, the present invention assists older children, teenagers, or adults who may be suffering from mental or physical disabilities such as down syndrome, autism, ADD/ADHD, tourettes, cerebral palsy, epilepsy. Alzheimer's, dementia, being paralyzed, etc. and who must wear diapers. The present invention is a valuable aid to hold and assist in applying a clean diaper to an individual.

The diapering assistance system of the present invention can be used by individuals from three months through elderly seniors who wear pull up diapers. For those older individuals, the user can change into a clean diaper easily with the help of the present invention without removing clothes from the waist down. It will allow them to apply a diaper with ease in a flat fold diaper manner.

These and other objects are accomplished by the present invention, a diapering assistance system which comprises a diaper, a diaper holding member which retains the top end of the diaper and suspends the bottom end of the diaper. A belt member is attached to the diaper holding member for encircling the waist of the individual being diapered. The belt member has connection devices, such as hook and loop connectors or their equivalents, and constitutes the sole component used for attaching the system to the individual. The method of use includes securing the top end of the diaper to the diaper holding member, suspending the diaper therefrom and behind the individual to be diapered and encircling the individual with the belt element and securing it around the waist of the individual. The bottom end of the diaper is then lifted between the legs and to the front of the individual. The diaper is then attached to the individual and the diaper holding member and belt member are removed.

The novel features which are considered as characteristic of the invention are set forth in particular in the appended claims. The invention, itself, however, both as to its design, construction and use, together with additional features and advantages thereof, are best understood upon review of the following detailed description with reference to the accompanying drawings.

BRIEF DESCRIPTION OF THE DRAWINGS

FIG. 1 is a rear plan view of the belt member and diaper holding member of the present invention, with the first flap section of the diaper holding member extended over the belt member.

FIG. 2 is a front plan view of the belt member and the diaper holding member, with the first flap section partially folded over the second flap section.

DETAILED DESCRIPTION OF THE INVENTION

Figure 3:
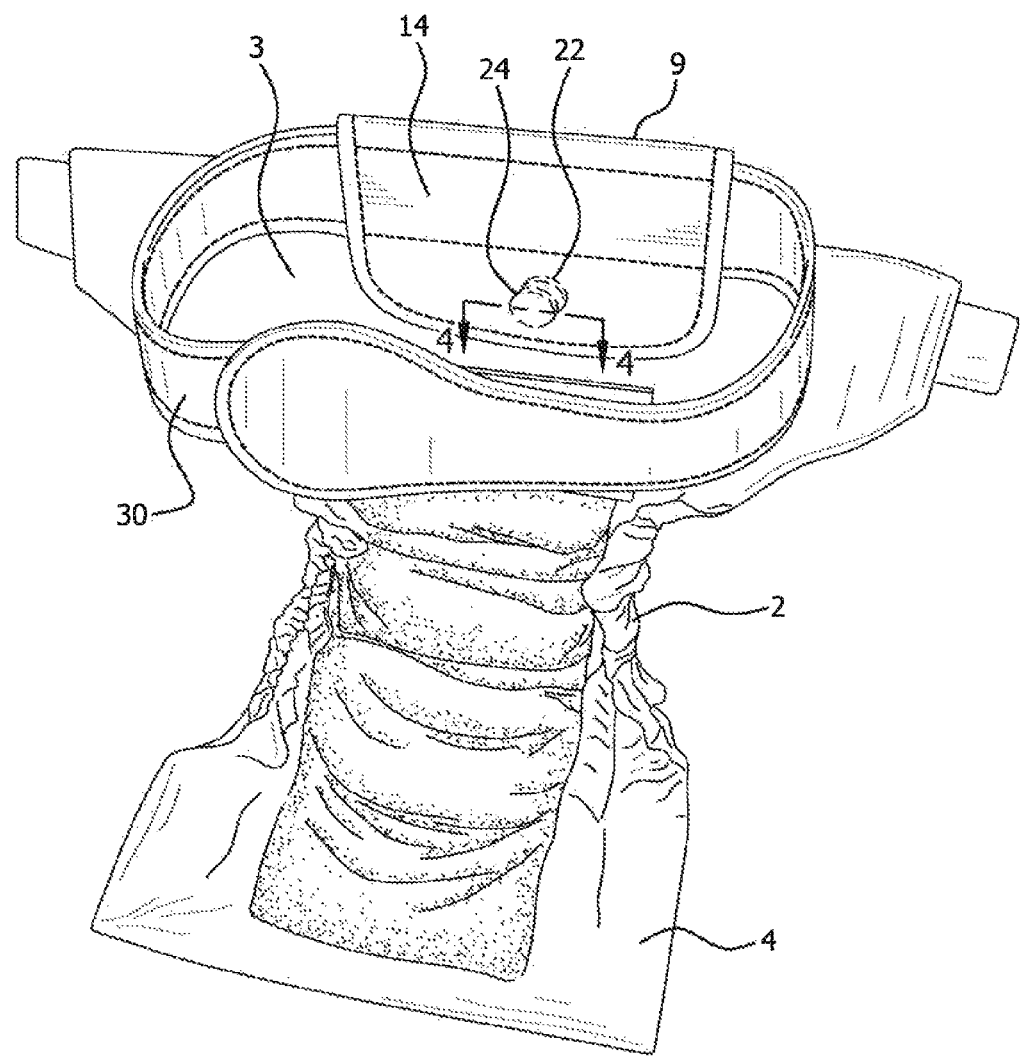
FIG. 3 is a perspective view of a diaper secured to the diaper holding member, with the belt member ends connected.

The diapering assistance system 1 of the present invention comprises diaper 2, having top end 3 and bottom end 4, and diaper holding member 5 having first flap section 6 and second flap section 14. These flap sections are rotatably connected by fold joint 9.

Figure 4:
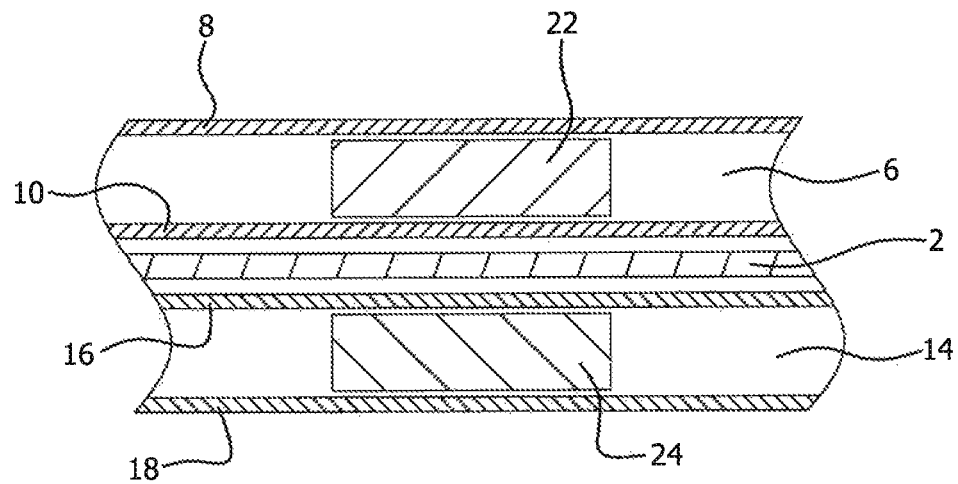
FIG. 4 is a cross-sectional view taken from FIG. 3.

As best seen in FIGS. 1 and 4, first flap section 6 comprises layers 8 and 10 made of flexible, waterproof plastic or equivalent material, sewn together at 12. Logo patch 23 is provided on layer 8. Similarly, second flap section 14 is made of the same material as first flap section 6 and comprises layers 16 and 18 sewn together at 20. Magnet 22 is located between layers 8 and 10 of first flap section 6, for attraction to magnet 24 located between layers 16 and 18 of second flap section 14, when the flap sections are folded down on each other. Magnets 22 and 24 provide the means to fixedly maintain diaper 2 between first flap section 6 and second flap section 14.

Belt member 30, preferably made of the same waterproof material as flap sections 6 and 14, is attached at its midpoint, by sewn or equivalent connection 32, to flap sections 6 and 14. Velcro® or like loop and hook connectors 34 and 36 are provided at ends 38 and 40 of belt member 30. Connectors 34 and 36 extend a sufficient length to allow the length of belt member 30 to be adjustable, depending on the size of the waist of the individual wearing the belt member and receiving diaper 2. It is contemplated that belt member 30 can also use a belt and buckle arrangement, seat belt type tab insertion attachment system, or their equivalents to adjustably set the length of the belt member.

Figure 5:
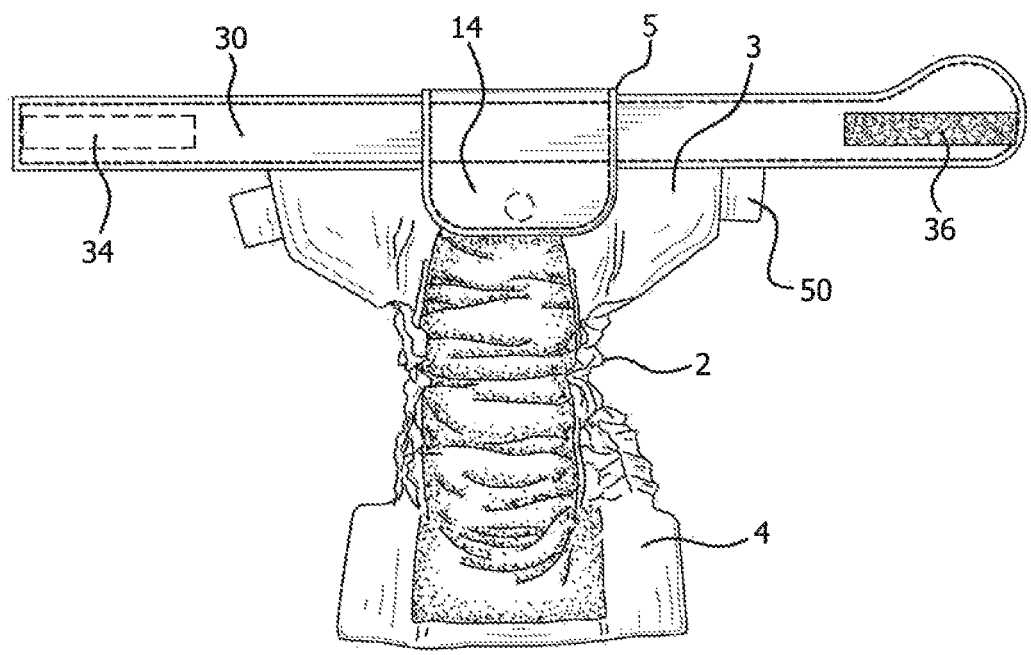
FIG. 5 is another view of a diaper secured to the diaper holding member, with the belt member fully extended.
Figure 6:
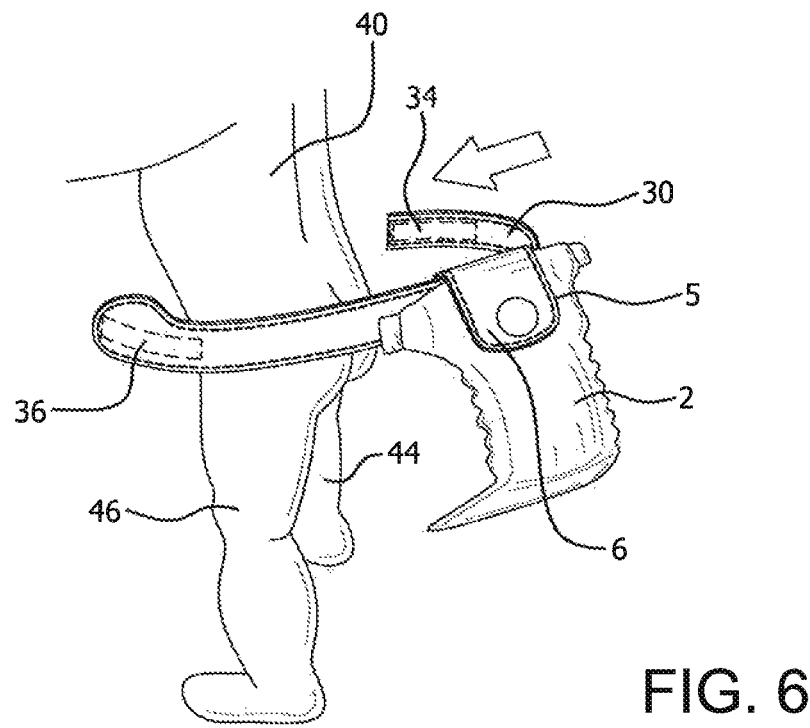
FIGS. 6-9 illustrate the steps of the method of use of the present invention.
Figure 8:
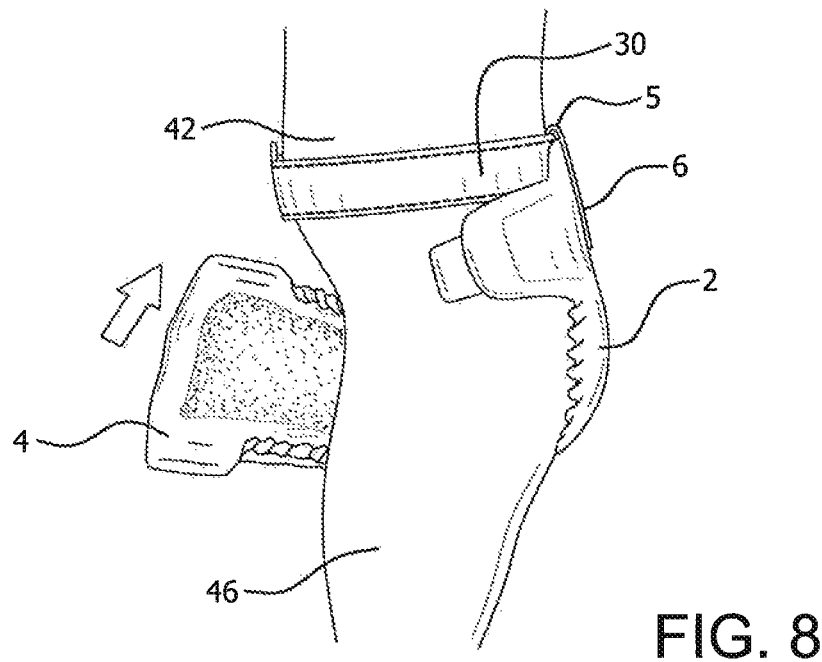

Diapering assistance system 1 is utilized as follows. Diaper holding member 5 is placed in the open position, that is with its first flap section 6 extended above second flap section 14, as seen in FIG. 1. Top end 3 of diaper 2 is positioned on layer 16 of second flap section 14 and first flap section 6 is then folded over top end 3 of diaper 2. FIG. 2 shows first flap section 6 partially folded to receive the diaper. Once top end 3 of diaper 2 is inserted between flap sections 6 and 14, magnets 22 and 24 are caused to attract, thus maintaining the top end of the diaper secured to diaper holding member 5 and suspending bottom end 4 of the diaper, as depicted in FIGS. 3 and 5. These FIGs. show the diaper secured between second flap section 14 and first flap section 6, not seen in FIG. 3, but located over the diaper. FIGS. 6 and 8 best show the position of first flap section 6 in securing diaper 2.

Figure 7:
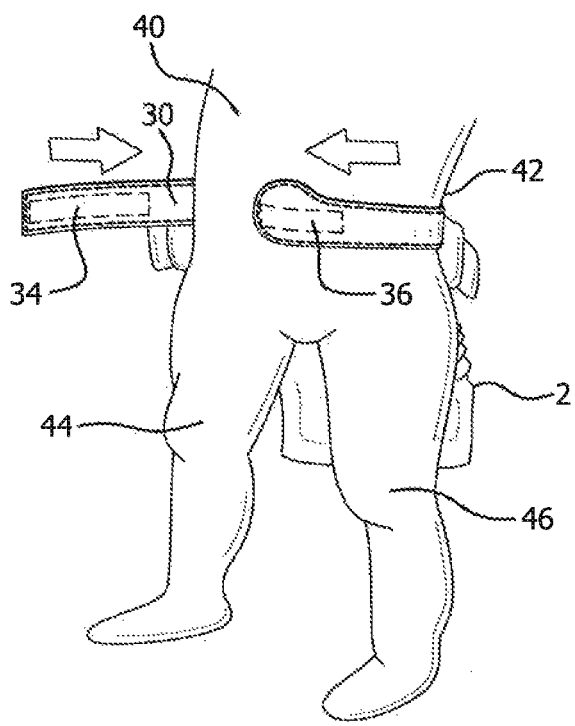
Figure 9:
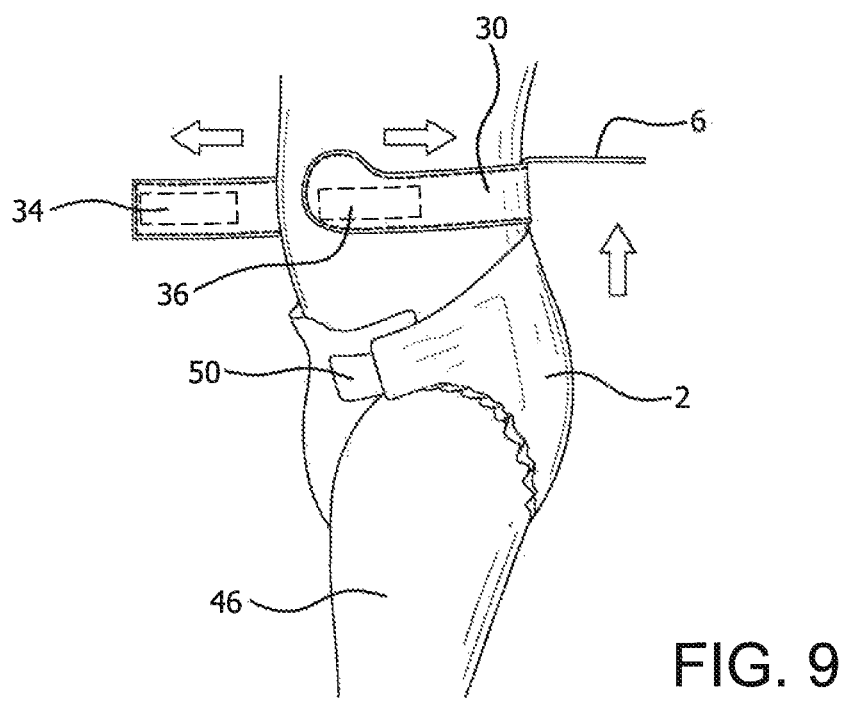

Diaper 2 is then positioned and suspended behind the baby or adult individual 40 receiving the diaper, and belt member 30 is encircled around waist 42 of individual 40 and secured in this position by connectors 34 and 36, which are adjustable to fit the individuals waist size. See FIGS. 6 and 7. Bottom end 4 of diaper 2 is then lifted between legs 44 and 46 and adjacent to the front of individual 40, as shown in FIG. 8, where the diaper is attached to the individual by the usual diaper tab means 50. First flap section 6 is lifted up and off second flap section 14 of diaper holding member 5, in order to remove the diaper holding member from diaper 2. Connectors 34 and 36 are then detached and belt member 30 is removed from individual 40, who is now securely diapered. See FIG. 9.

Diapering assistance system 1 is thus easily utilized and secured when an individual or baby is standing or, in case of a baby, also in a crawling position. It allows a baby, child or adult a diapering change in a clean and efficient manner, easily and quickly without the need to remove pants or shoes.

The belt member can be manufactured in a number of sizes, adapted to fit various different sized individuals. The versatility of the system even makes it readily adaptable for use on domestic animals, such as dogs and cats.

Certain novel features and components of this invention are disclosed in detail in order to make the invention clear in at least one form thereof. However, it is to be clearly understood that the invention as disclosed is not necessarily limited to the exact form and details as disclosed, since it is apparent that various modifications and changes may be made without departing from the spirit of the invention.

The invention claimed is:

1. A system for assisting in diapering an individual comprising:

a diaper having a top end and a bottom end;

a single component diaper holding member for retaining the top end of the diaper and for suspending the bottom end of the diaper below the top end, said integral diaper holding member comprising first and second flap sections connected to each other solely by a fold joint, said flap sections being foldable from an open position in which the first flap section extends above the second flap section, to a second position wherein the first flap section is folded down over the second flap section with the top end of the diaper located and maintained between the first and second flap sections;

a single component belt member of given continuous length, said belt member being attached at its midpoint to the diaper holding member and for encircling the individual being diapered, the belt member being the sole component attaching the system to said individual; and means to secure the belt member around the individual, whereby the diaper is deployable from a hanging position in which the diaper is suspended from the diaper holding member and the belt member to a raised position in which the diaper is located adjacent to the front of said individual.

2. The system as in claim 1 wherein the means to secure the belt member is adjustable in order to change the length of the belt member.

3. The system as in claim 1 wherein the belt member has two ends and is permanently attached to the diaper holding member between said ends.

4. The system as in claim 1 further comprising means located within each flap section to maintain the top end of the diaper between the flap sections in the raised position.

* * * * *